United States Patent [19]

Esbenshade

[11] Patent Number: 4,556,555
[45] Date of Patent: Dec. 3, 1985

[54] PROCESS FOR THE IMMUNOLOGICAL NEUTERING OF ANIMALS

[75] Inventor: Kenneth L. Esbenshade, Raleigh, N.C.

[73] Assignee: North Carolina State University, Raleigh, N.C.

[21] Appl. No.: 694,695

[22] Filed: Jan. 25, 1985

[51] Int. Cl.$^4$ .................... A61K 39/395; A61K 37/38
[52] U.S. Cl. ........................ 424/85; 514/21; 424/101
[58] Field of Search ........................ 424/85, 101, 177; 514/21

[56] References Cited

U.S. PATENT DOCUMENTS

| | | | |
|---|---|---|---|
| 4,161,519 | 7/1979 | Talwar | 424/85 X |
| 4,196,123 | 4/1980 | Rosemberg | 424/177 |
| 4,271,069 | 6/1981 | Tsong et al. | 424/177 X |
| 4,338,305 | 7/1982 | Corbin | 424/177 |
| 4,377,574 | 3/1983 | Rivier et al. | 424/177 |
| 4,384,995 | 5/1983 | Stevens | 424/85 X |

*Primary Examiner*—Howard E. Schain
*Attorney, Agent, or Firm*—Bell, Seltzer, Park & Gibson

[57] ABSTRACT

A process for the passive neutering of animals is provided in which pre-pubertal animals are treated to prevent the on-set of puberty by introducing into their bloodstreams an antiserum containing antibodies to gonadotropin releasing hormone so as to immunize the pre-pubertal animals against the gonadotropin releasing hormone to prevent thereby the release of hormones necessary for sexual development.

14 Claims, No Drawings

PROCESS FOR THE IMMUNOLOGICAL NEUTERING OF ANIMALS

The present invention relates to the neutering of animals and particularly to the neutering of animals by a process of immunization.

BACKGROUND OF THE INVENTION

The neutering of certain animals is desirable for a great variety of reasons. Certain animals are used primarily as pets and the indiscriminant reproduction by such animals has created problems for animal control agencies and grave concerns by others.

Other animals are used primarily as a source of meat and neutering of such animals is desirable since reproductive functions by such animals are unnecessary and in many instances undesirable. For example, the meat of certain reproductively active male animals (such as male pigs or boars) has an objectionable odor and unpleasant taste which makes the meat unacceptable to consumers. The source of this odor and taste is a compound produced from testosterone (the major sex steroid in males) which saturates such meat. The only known procedure for providing consumer acceptable meat from such male animals is castration at a time sufficiently prior to slaughter such that testosterone production is halted and the compound producing the objectionable odor and unpleasant taste has been removed from the meat of the neutered animal by natural body functions.

It is conventional practice in the swine industry, and certain other meat production industries, to castrate all males intended for meat production and this procedure is usually performed when the males are from 7 to 14 days old. Such castration is currently accomplished in the swine industry by a surgical procedure to which there are several objections. Firstly, such surgical procedures greatly increase the likelihood of infection and may cause other health problems. Secondly, some have raised objections to such surgical procedures contending that they are inhumane.

For the foregoing reasons, it is an object of the present invention to provide for the neutering of animals without the necessity of a surgical procedure and in a manner to which objections for humane reasons would not be raised.

A more specific object of the present invention is to provide a process for the immunological neutering of animals which is simple, safe and effective.

Gonadotropin releasing hormone, a peptide hormone produced in the brain of animals, controls reproductive functions by influencing the synthesis and release of hormones from the pituitary gland necessary for sexual development, maintenance and reproduction. It has been previously proposed that an immunological response could be obtained by combining gonadotropin releasing hormone with a foreign protein and injecting certain animals with this combination. In this regard, experiments involving the injection of adult male rabbits, adult male rats, adult male and female monkeys and adult ewes with gonadotropin releasing hormone combined with a foreign protein have been reported. According to such reports, repeated injections of this combination have caused a noticeable decline in luteinizing hormone and follicle-stimulating hormone as well as testicular regression due to atrophy of the testes and secondary sex organs and an end to ovarian cycles.

While recognizing the immunological reaction, these previous experiments have not resulted in any acceptable techniques or procedures that could be utilized as a solution to the aforementioned problem. These reported experiments require repeated injections over a considerable time period (up to 12 months in some cases) and the results achieved were mixed.

SUMMARY OF THE INVENTION

The present invention provides a process by which animals may be passively neutered without surgery and by a simple procedure that is completely effective. This procedure comprises treating pre-pubertal animals to prevent the on-set of puberty by introducing previously collected antibodies to gonadotropin releasing hormone into the bloodstream of the animals. The antibodies immunize the pre-pubertal animals against gonadotropin releasing hormone resulting in non-detectable levels of luteinizing and follicle-stimulating hormones. Consequently, the animals will not develop sexually and the on-set of puberty will be prevented. Accordingly, testosterone, estrogen and progesterone necessary for male and female animals to be reproductively active will not be produced.

DETAILED DESCRIPTION OF THE INVENTION

The present invention will be described as it applies to meat-producing animals, particularly swine, but it should be understood that this invention may be applicable to other animals. Therefore, the following description should be considered as illustrative rather than limiting.

Neonatal pigs acquire immunity from their dam by the absorption of immunoglobulins from colostral milk (first milk) during the first 24–36 hours after birth. Research has shown that, even during this period, the brain, pituitary and testes of the neonatal male pig are actively secreting hormones, and this hormonal activity is a prerequisite for normal sexual development later in life.

The present invention utilizes antibodies to gonadotropin-releasing hormone that have been collected from other animals of the same species. These antibodies are produced by such other animals as an immunological response to injections of gonadotropin releasing hormone combined or conjugated with a foreign protein (e.g. bovine serum albumin). Following initial immunization and several boosters, antibodies are collected from the treated animals by withdrawing blood from the treated animals and an antiserum containing such antibodies is prepared from this blood by known procedures.

This antiserum is preferably mixed with an aqeous suspension of milk solids with equal parts of antiserum and suspension. For example, this suspension may contain 20% (W/V) of milk solids and the antiserum may have a titre of 1:70,000 (1:230,000 on a milliliter basis). A predetermined amount, preferably between 20 and 25 milliliters, of this antiserum and suspension is introduced into the digestive tract of the new-born pigs while their digestive tracts are capable of absorbing the antibodies, i.e. within 24 to 36 hours after birth. It is preferred that this solution be introduced into the stomach by a stomach tube as the first ingestion after birth.

In experiments to date, 7 baby male pigs were treated with 20 milliliters of milk solid suspension and antiserum (10 ml of 20% milk solid suspension and 10 ml of antiserum having a titre of 1:70,000) within the first 24 to 36 hours after birth by introduction into the digestive tract by stomach tube. Controls were similarly treated with 20 ml of milk solid suspension alone. The treatment of the controls has resulted in no response while the treatment of the neonatal pigs with the antiserum has resulted in markedly depressed sexual development.

The foregoing embodiments and examples are to be considered illustrative, rather than restrictive of the invention, and those modifications which come within the meaning and range of equivalence of the claims are to be included therein.

That which is claimed is:

1. A process for the immunological neutering of animals comprising
treating pre-pubertal animals to prevent the onset of puberty by introducing into the bloodstreams of the animals a predetermined amount of an antiserum containing antibodies to gonadotropin releasing hormone so as to immunize the animals against gonadotropin releasing hormone to prevent thereby the release of hormones necessary for sexual development.

2. A process according to claim 1 wherein the animals being neutered are capable of passing the antibodies through the intestinal walls into the bloodstream, and wherein said antiserum is introduced into the digestive tract of the animal.

3. A process according to claim 1 wherein the antibodies contained in said antiserum are antibodies produced by another animal of the same species previously injected with gonadotropin-releasing hormone combined with a foreign protein.

4. A process according to claim 1 wherein the animal being neutered is of a species of animal primarily utilized for meat production.

5. A process according to claim 1 in which the treatment of the pre-pubertal animals occurs while the animals are in the neo-natal stage and before appreciable sexual development has occurred.

6. A process for the immunological neutering of animals comprising
   (a) providing an antiserum containing antibodies to gonadotropin releasing hormone produced by another animal previously injected with gonadotropin releasing hormone combined with a foreign protein, and
   (b) treating pre-pubertal animals while in the neonatal stage to prevent the on-set of puberty by introducing into the bloodstreams of the animals a predetermined amount of said antiserum so as to immunize the animals against gonadotropin releasing hormone to prevent thereby the release of hormones necessary for sexual development.

7. A process according to claim 6 wherein the animals being neutered are capable of passing the antibodies to gonadotropin releasing hormone through the intestinal walls into the bloodstream, and wherein said antiserum is introduced into the bloodstream by ingestion through the digestive tract.

8. A process according to claim 6 wherein the introduction of said antiserum into the bloodstream is by intravenous injection.

9. A process for the immunological castration of male piglets comprising the steps of:
   (a) providing an antiserum containing antibodies to gonadotropin releasing hormone, and
   (b) treating each male piglet to prevent the onset of puberty by introducing into the digestive tract thereof a predetermined amount of said antiserum so that the antibodies in said antiserum pass through the walls of the intestines and into the bloodstream to immunize the piglets against gonadotropin releasing hormone so as to prevent the release of hormones necessary for sexual development of the piglets.

10. A process according to claim 9 wherein the male piglets are caused to ingest said antiserum during the neonatal period after birth.

11. A process according to claim 9 wherein the step of providing antiserum includes collecting antibodies from adult swine previously injected with gonadotropin releasing hormone attached to a foreign protein.

12. A process for the immunological castration of male piglets comprising the steps of:
   (a) providing an antiserum containing antibodies to gonadotropin-releasing hormone produced by another swine previously injected with gonadotropin releasing hormone combined with a foreign protein, and
   (b) treating each male piglet within the first 24 to 36 hours after birth to prevent the on-set of puberty by introducing into the digestive tract thereof a predetermined amount of said antiserum so that the antibodies in said antiserum pass through the walls of the intestines and into the bloodstream so as to immunize the male piglets against gonadotropin releasing hormone to prevent the release of hormones necessary for sexual development of the piglets.

13. A process according to claim 12 wherein said antiserum is mixed in equal parts with an aqueous solution of milk solids.

14. A process according to claim 13 wherein said antiserum is introduced by use of a stomach tube.

* * * * *